United States Patent
Gilson et al.

(10) Patent No.: US 8,024,049 B1
(45) Date of Patent: Sep. 20, 2011

(54) SPATIAL-TEMPORAL DEEP BRAIN STIMULATION METHODS AND SYSTEMS

(75) Inventors: Richard D. Gilson, Oviedo, FL (US); Nizam Razack, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 782 days.

(21) Appl. No.: 10/969,420

(22) Filed: Oct. 20, 2004

Related U.S. Application Data

(60) Provisional application No. 60/512,660, filed on Oct. 20, 2003, provisional application No. 60/586,468, filed on Jul. 8, 2004.

(51) Int. Cl.
*A61N 1/36* (2006.01)

(52) U.S. Cl. ............ 607/139; 607/45; 607/62; 607/116

(58) Field of Classification Search ............ 607/62, 607/139, 45, 116
See application file for complete search history.

(56) References Cited

U.S. PATENT DOCUMENTS

| | | | |
|---|---|---|---|
| 3,628,538 A * | 12/1971 | Vincent et al. ............ 607/62 |
| 5,474,574 A * | 12/1995 | Payne et al. ............ 607/7 |
| 5,479,934 A * | 1/1996 | Imran ............ 600/544 |
| 5,707,396 A | 1/1998 | Benabid ............ 607/2 |
| 5,716,377 A | 2/1998 | Rise et al. ............ 607/2 |
| 5,833,709 A | 11/1998 | Rise et al. ............ 607/2 |
| 6,038,480 A | 3/2000 | Hrdlicka et al. ............ 607/116 |
| 6,301,492 B1 | 10/2001 | Zonenshayn ............ 600/378 |
| 6,366,813 B1 | 4/2002 | DiLorenzo ............ 607/45 |
| 6,539,263 B1 | 3/2003 | Schiff et al. ............ 607/45 |
| 6,597,954 B1 * | 7/2003 | Pless et al. ............ 607/62 |
| 6,618,623 B1 * | 9/2003 | Pless et al. ............ 607/45 |
| 2002/0013612 A1 * | 1/2002 | Whitehurst ............ 607/45 |
| 2002/0183817 A1 | 12/2002 | Van Venrooij et al. ....... 607/116 |
| 2002/0188330 A1 | 12/2002 | Gielen et al. ............ 607/45 |
| 2003/0023297 A1 | 1/2003 | Byers et al. ............ 607/141 |
| 2003/0085684 A1 | 5/2003 | Tsukamoto et al. ........ 320/108 |
| 2003/0130706 A1 * | 7/2003 | Sheffield et al. ............ 607/46 |
| 2003/0181954 A1 | 9/2003 | Rezai ............ 607/45 |
| 2004/0172090 A1 * | 9/2004 | Janzig et al. ............ 607/45 |
| 2004/0176814 A1 * | 9/2004 | Singhal et al. ............ 607/45 |
| 2005/0143790 A1 * | 6/2005 | Kipke et al. ............ 607/60 |
| 2005/0159799 A1 * | 7/2005 | Daglow et al. ............ 607/116 |
| 2005/0171587 A1 * | 8/2005 | Daglow et al. ............ 607/116 |

* cited by examiner

*Primary Examiner* — Carl H Layno
*Assistant Examiner* — Jennifer Stewart
(74) *Attorney, Agent, or Firm* — Brian S. Steinberger; Law Offices of Brian S. Steinberger, P.A.

(57) ABSTRACT

Methods, systems, and devices to reduce power demands substantially for current deep brain stimulation DBS using smart technology type applications. The invention uses miniaturized components that allow integration with the implanted probe(s) themselves, and includes a skull-sited housing having all the controls and battery power supply needed. This avoids implanting obtrusive card-deck size batteries in the chest area and the use of vulnerable wire leads under the skin from the chest area to connect with the implanted electrode(s) on the skull, improving comfort. The Generating of non-continuous pulses on demand of conditions such as the occurrence of a tremor occurs, without having to continuously run pulses at all times, substantially increasing life spans over current techniques. Shaped electrodes and their methods further reduce power demands and efficacy by directing electric fields to focus towards specific areas and regions of the brain rather than inefficient 360-degree emission.

18 Claims, 12 Drawing Sheets

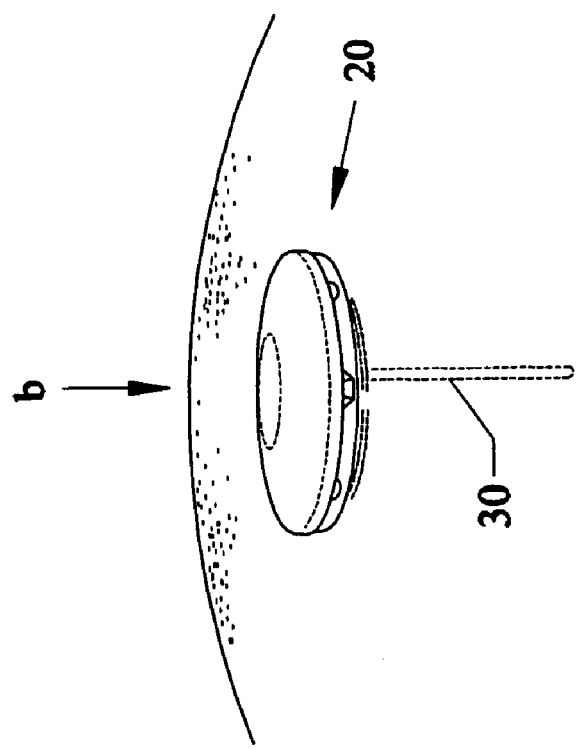
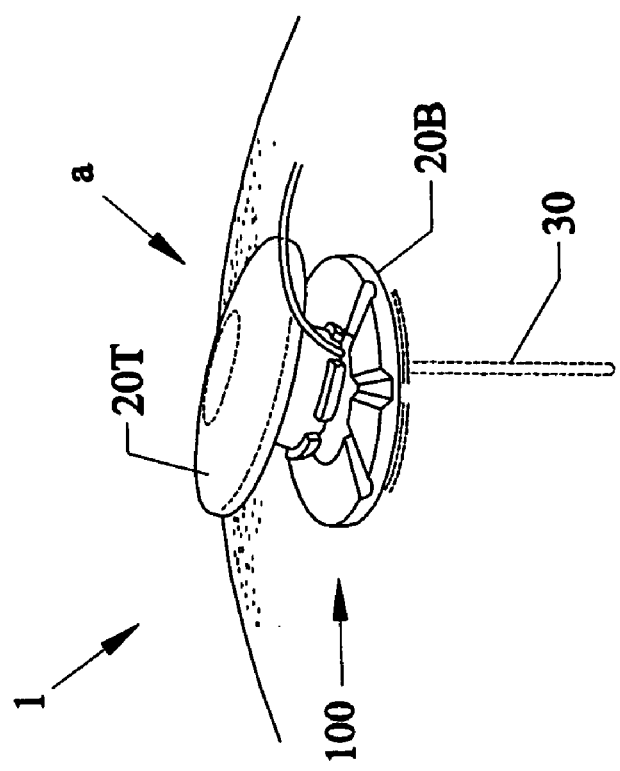

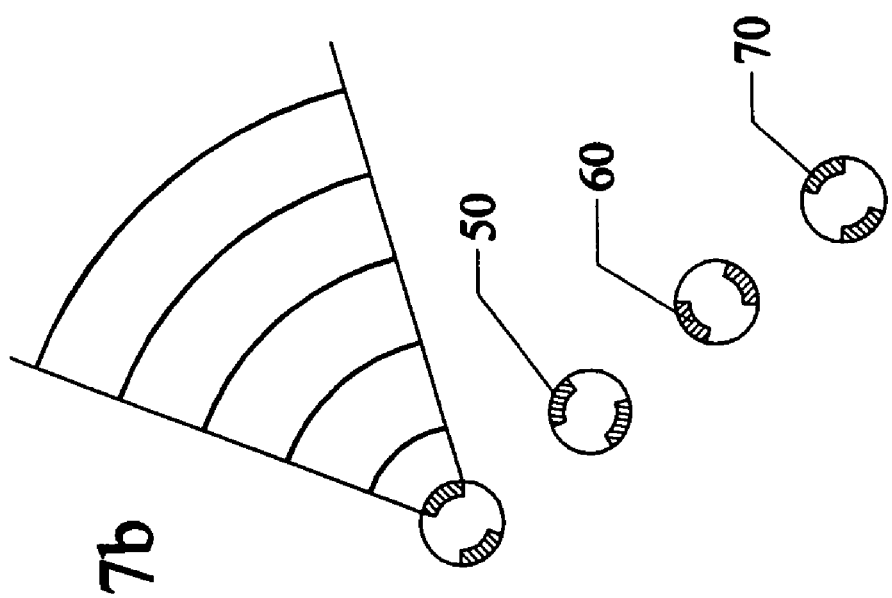
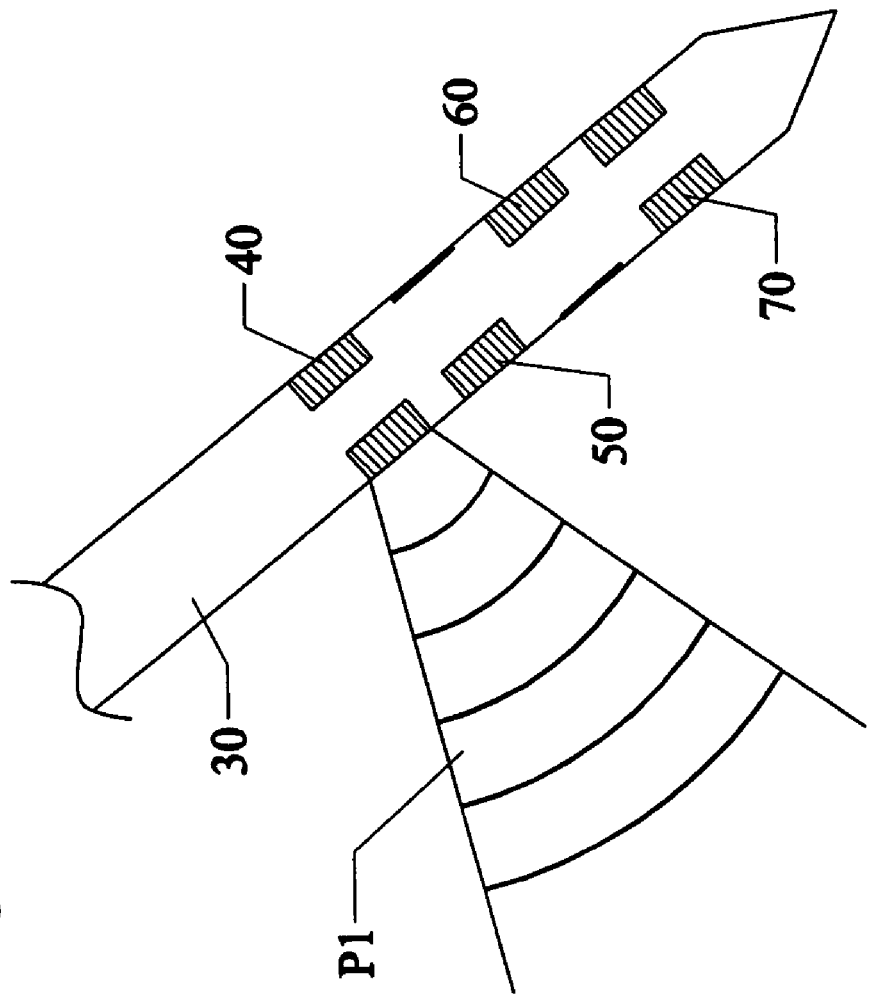

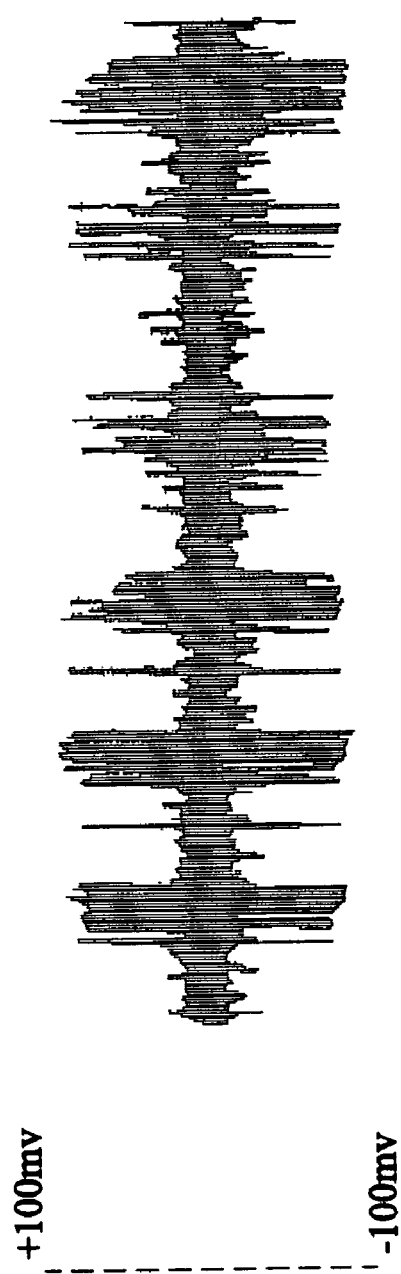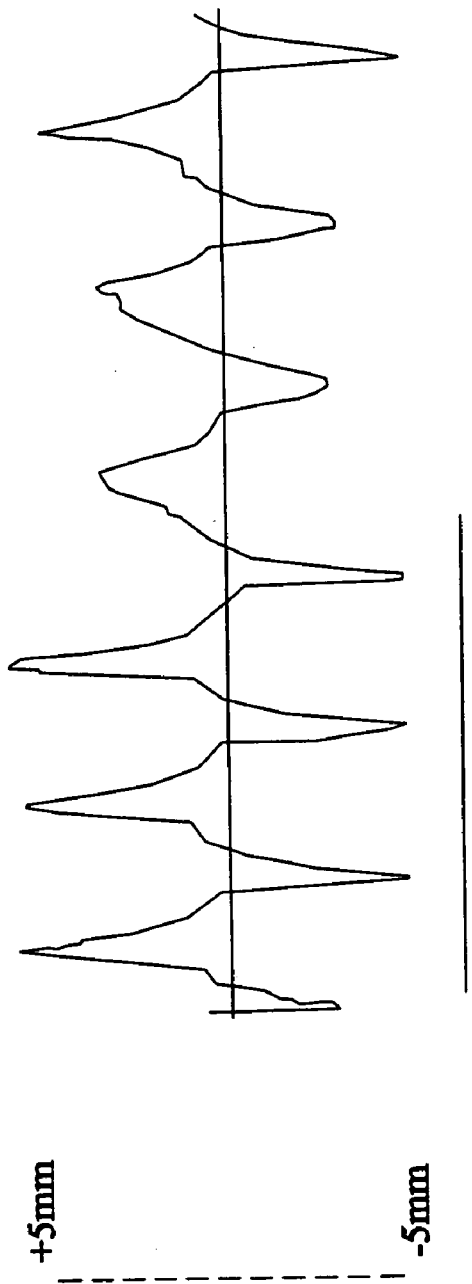

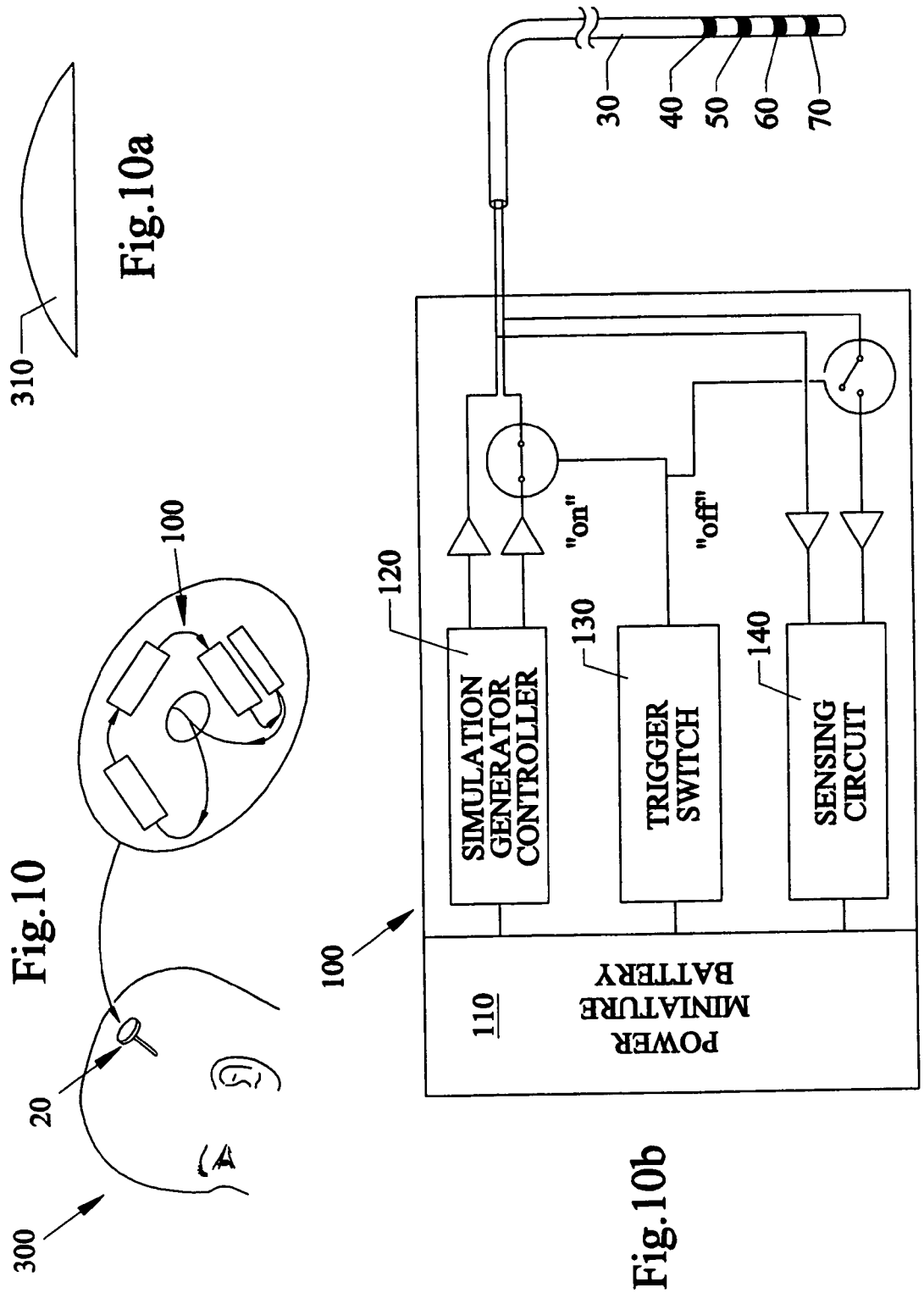

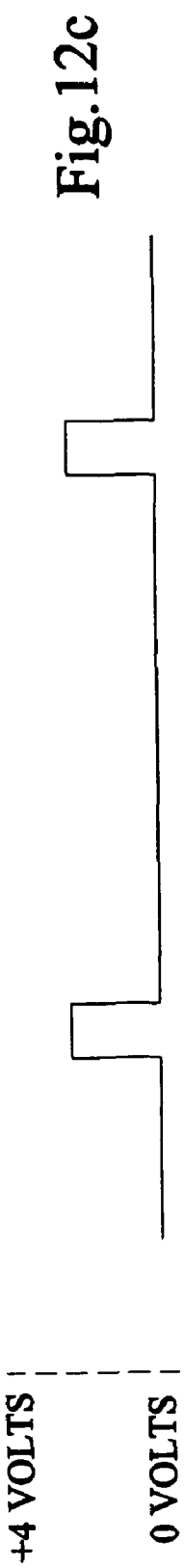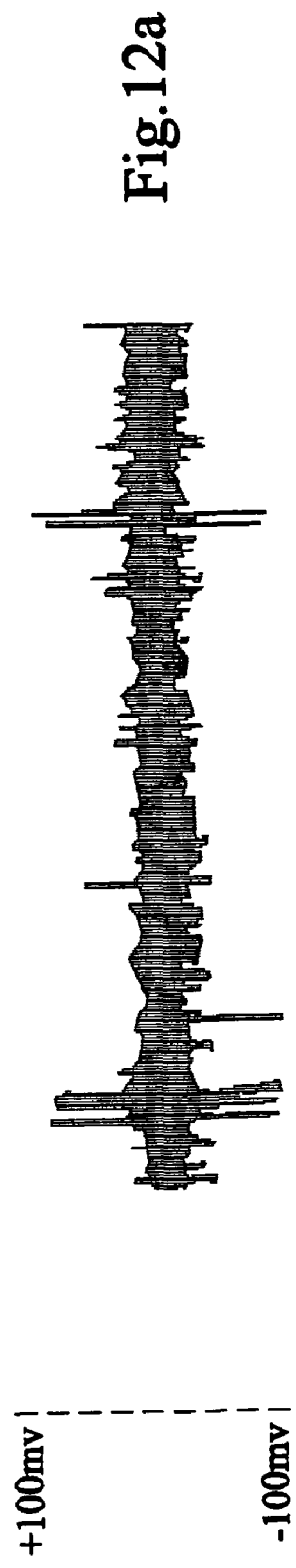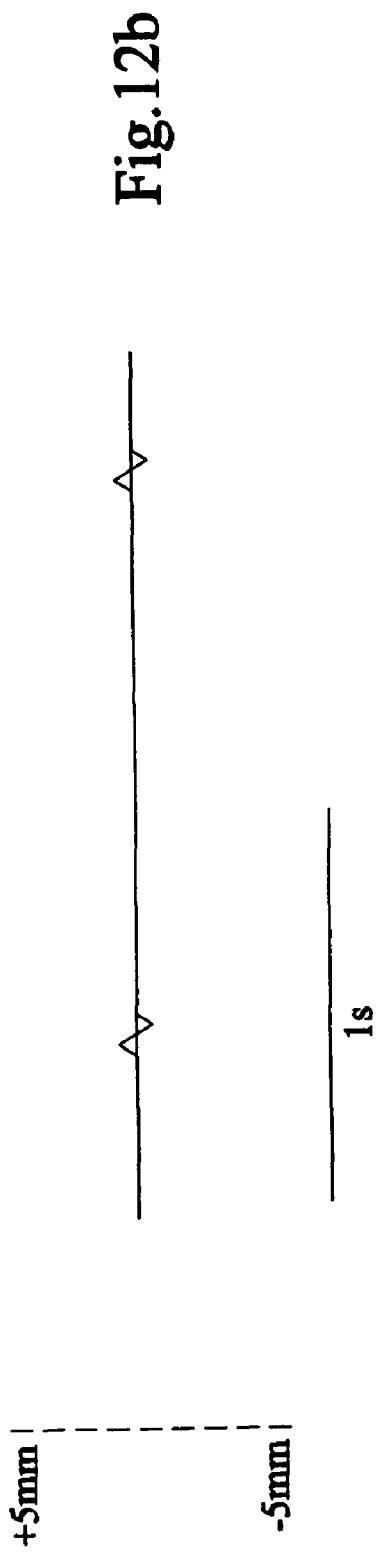

SPATIAL-TEMPORAL DEEP BRAIN STIMULATION METHODS AND SYSTEMS

This invention claims the benefit of priority to U.S. Provisional Patent Application Ser. Nos. 60/512,660 filed Oct. 20, 2003, and 60/586,468 filed Jul. 8, 2004.

FIELD OF INVENTION

This invention relates to deep brain stimulation (DBS), in particular to methods, systems, and devices for enhancing both efficacy and efficiency of "in-vitro" electrical stimulation known to inhibit symptoms of neurological diseases, disorders, and the like, and utilizes: (a) methods that tailor the direction and shape of electrical fields towards the area of best effect; (b) systems that interactively trigger stimulation to terminate the onset of tremors, and such; and (c) devices that use the aforementioned efficiencies to reduce power and allow for self-contained miniaturization at the implant site, thereby improving patient comfort.

BACKGROUND AND PRIOR ART

A first line of defense considered for most neurological disorders is treatment with psychoactive medicines, prior to any surgical intervention. Psychoactive medicines or drugs are those capable of acting on the nervous system and affecting mental states and behavior. Many physiological mechanisms are aided by such drugs, but these medicines have unwanted side effects, drug interactions, and long-term physiological tolerances that render the drug less effective over time.

In the case of Parkinson's disease that serves as the exemplar disorder herein, the underlying etiology is that neurons, located in the substantia nigra of the mid-brain, for some unknown reason begin to produce less dopamine. As these neurons progressively and relentlessly deteriorate over years, less dopamine dramatically affects the motor control of the basal ganglia and thus outward behavior and everyday living. An estimated 1.5 million Parkinson's patients have a visible cluster of diagnostically significant and debilitating Parkinson's symptoms, typically tremors, stiffness, slowness, and balance. Patients describe the internal feeling as frozen still in the "set" stage of the "ready, set, go" sequence that started of a race.

The "gold" standard treatment for Parkinson's is frequent daily administration of an indirect dopamine replacement, L-Dopa, a psychoactive drug that crosses the blood-brain barrier, and then alters form to produce dopamine as a supplement to the brain's own production. This therapy, while initially quite beneficial, typically can lose much of its effectiveness over about five years, wherein patients have to take progressively larger and more frequent doses until eventually the result becomes inadequate. Without alternative drug therapies, patients are left to suffer both the ravages of primary symptoms and the manifestations resulting from the prolonged use of the drug itself, principally the repetitive spasmodic motions of dyskinesia. More than one million people endure these symptoms, including such notables as the Pope, Muhammad Ali, and Billy Graham, while thousands of others including Michael J. Fox have turned to surgical approaches.

Past surgical techniques treated symptoms of these diseases by selectively and permanently destroying or ablating structural areas in the brain. The net effect is to "shut the door", in a neurological fashion, before dysfunctional brain signals are sent to the muscles, thereby relieving many symptoms. The advantage of surgical ablation is that it reduces the reliance on drug therapy with its attendant side effects. The disadvantage is that the procedure is irreversible. This may render such patients as unacceptable candidates for newly discovered techniques/therapies, such as stem cell implantation or viral transport of genome-altered DNA (deoxyribonucleic acid), both of which show promise in helping to augment or even to regenerate the natural production of dopamine as well as a number of other substances involved in neurological disorders.

Certain neurological disorders that produce debilitating motor symptoms are now being treated with Deep Brain Stimulation (DBS) through-skull implanted electrodes see FIG. 1 below. DBS essentially reversibly alters the local neurological structure(s) around the tip of an electrode implanted on the brain with electrical pulses that reduce or stop disabling symptoms, such as, but not limited to, severe tremor and rigidity found in Parkinson's disease.

DBS functionally has the advantage of emulating ablation by changing the firing characteristics of nearby neurons, but it does so only while the pulsed stimulation persists. Since the structures remain intact and undamaged, when DBS is turned "off" these structures reactivate and symptoms return, unless otherwise treated. Thus, DBS overcomes the chief disadvantage of ablation in that it allows implanted simulators to be withdrawn later for new techniques, with minimal residual effects. In 1998, the Federal Drug Administration (FDA) approved DBS as an alternative for, or as an adjunct to powerful psychoactive drugs (neuro-medicines) burdened with strong and often unacceptable side effects.

The only FDA approved DBS apparatus is currently being sold by Medtronic, Inc., 710 Medtronic Parkway, Minneapolis, Minn. 55432-560, see FIGS. 2 and 3 below, although other companies have substantial interests in implantable neurostimulation devices for a variety of neurological disorders, such as Advanced Bionics, Corp., 12740 San Fernando Road, Sylmar, Calif. 91342; see "http://www.advanced bionics.com." However, there are problems with the approved apparatus.

At the very least, the presently approved apparatus is cumbersome and uncomfortable for many in its present form. As an outgrowth of legacy components from heart "pacemakers," it consists of one or two remote stimulator/battery packs embedded under muscle tissue in the upper chest area, and requires subcutaneous leads up along the neck to the skull entry point. All these components are subject to corrosion and breakage, as well as to resistance or attacks by the body itself attempting by encapsulate it or dissolve it, leading to infection.

Medtronic currently uses a product called a Soletra™ Neurostimulator (see FIG. 4 below) to generate a continuous series of electrical pulses, typically at about 2-4 volts, to electrode(s) implanted in specific brain areas. Neurons, normally operating in the tens of milli-volts range, are massively over-stimulated by such voltage and temporally altered, thereby inhibiting the expression of certain motor dysfunctions. Pulse voltage is usually adjusted somewhat depending on the proximity of the electrode(s) to the targeted area, e.g., more voltage is needed for target variations. Typical pulse rates range around 130-185 pulses/second.

This combination of large amounts of voltage, amperage, and duty cycle creates a power drain that normally requires a non-renewable battery replacement in about 3-5 years, at a price of about $10,000. Many patients turn "off" the stimulation when going to sleep while tremor is quelled, in order to conserve power. Current DBS stimulator(s) are designed to be turned "off" or "on" using a magnetic-switch placed briefly near the associated electronics.

Thus, without considering the remote apparatus itself, or the power requirements of the present design, a goal in this field should be to reduce stimulation-related side effects and complications caused by stimulating in the vicinity of the target. Two key objectives to meeting that goal are for the surgical implant to hit the center of a targeted cellular region, often not more than 2 mm across in any direction, and for the current field to stimulate the appropriate cells for symptom reduction or cessation, without triggering side effects in adjacent structures.

While the surgical techniques themselves are well documented, the surgery is still a unique combination of art and science [see Lozano, Andres M. (Ed): Movement Disorder Surgery: Progress in Neurological Surgery, vol. 15, pp. 202-208, Basel, Switzerland: Karger AG, 2000, ISBN 3-8055-6990-4.].

A key to a successful outcome is the precise positioning and placement of the electrode(s), aided pre-operatively by vast improvements in brain imaging techniques, but nevertheless requiring considerable surgical skill and judgment. Beside normal variations in brain structures themselves adding to the difficulty of targeting, during surgery the brain moves with each heartbeat, while its size and position vary somewhat as a result of the surgical probe itself altering internal pressure. During the procedure, the use of fluoroscope imaging assists y-z axis positioning, and awakening of the patient while in the operating room for testing of clinical signs can reveal and help avoid untoward side effects. However, but the final outcome can only be assessed post-operatively. Results can vary by patient and over time. Some post-surgical adjustment is normally done with electrical parameters and z-axis programming of one or more of the electrode contacts available on the current DBS electrode, as is described below, but not to the extent that many physicians would like and not with respect to the x-y axis.

Current DBS electrodes have four (4) circumferential contacts that radiate current in a 360 degree configuration. This means that with any degree off-target, or unnecessary stimulation even on target adjacent cells are exposed to current and potential side effects. While some of these side effects may be adjustable when electrical parameters are altered, or even reversible when the stimulation is shut down, but the cost is decreased efficacy of stimulation on the symptoms. For example, in sub-thalamic nucleus DBS, stimulation-induced side effects may include increased dyskinesias, blepharospasm or so called "eyelid-opening apraxia," confusion/memory disturbances, personality changes, mood changes, apathy, cognitive changes, dysphonia/dysarthria, and such.

Medtronic Inc. has proposed a "Directional Brain Stimulation and Recording Leads, title, in U.S. Published Patent Application 2002/0183817 to Van Venrooij et al., which is incorporated by reference. The proposed technique uses a "controller" as shown and referenced to FIG. 32 for recording "brain activity signals" to activate electrodes. However, this technique requires continuously generating pulsed type signals once the electrodes are activated whether or not a brain type tremor has ended, which would result in needless, unwanted and potentially excessive electrical current being continuously generated inside the brain. The more unnecessary pulse type signals, the more undesirable side effects to the patient, for example, in thalamic DBS, stimulation-induced side effects may include paresthesias, muscular cramps, dystonia, dizziness, dysarthria, gait and balance disturbances, limb ataxia, impaired proprioception, and decreased fine motor movements.

Additionally, this technique would require excessive power to operate, which is not only expensive since battery power supplies would need to be regularly replaced but also require large card-deck size batteries that must be mounted inside of the patient's upper chest area. This proposed Medtronic technique would also be prone to circuit problems since the electrodes would be simultaneously operating as both transmitters and sensors, causing excessive and unnecessary power drain, shortening the lifespan of any batteries being used as well as increasing the costs for replacing the batteries.

According to the Movement Disorder Society ©2002, "Deep brain stimulation for the alleviation of movement disorders and pain is now an established therapy. However, very little has been published on the topic of hardware failure in the treatment of such conditions irrespective of clinical outcome. Such device-related problems lead to significant patient morbidity and increased cost of therapy in the form of prolonged antibiotics, in-patient hospitalization, repeat surgery, and device replacement [Joint, C., Nandi, D., Parkin, S., Gregory, R., and Aziz, T. *Hardware-Related Problems of Deep Brain Stimulation.* Movement Disorders, Vol. 17, Suppl. 3, 2002, pp. S175-S180.]

Thus, the need exists for solutions to the problems encountered in the prior art.

SUMMARY OF THE INVENTION

A first objective of the present invention is to provide for deep brain stimulation (DBS) methods, systems and devices that avoid implanting large card-deck size batteries remotely in the chest area and the use of vulnerable wire leads under the skin from the chest area to connect with the implanted electrode on the skull.

A second objective of the present invention is to provide for deep brain stimulation (DBS) methods, systems and devices that allow for substantially all electronics including but not limited to an on-site battery pack to be located at or near the implanted electrodes on the skull.

A third objective of the present invention is to provide for deep brain stimulation (DBS) methods, systems, and devices that can use substantially less power than current DBS techniques and apparatus.

A fourth objective of the present invention is to provide for deep brain stimulation (DBS) methods, systems and devices, that do not generate a continuous series of un-synchronized pulses that are continuously generated whether they are needed or not.

A fifth objective of this invention is to provide for deep brain stimulation (DBS) methods, systems and devices, to generate pulses on demand. Specifically, inhibiting pulse(s) can be interactively triggered by the onset of each unwanted electro-physiologically signaled event, such as at the beginning of a tremor.

A sixth objective of the present invention is to provide for deep brain stimulation (DBS) methods, systems and devices that are more compact, easier to use and last longer than current DBS techniques, thereby improving patient comfort.

A seventh objective of the present invention is to provide for shaped electrodes and methods by using the electrode contacts in deep brain stimulation (DBS) methods, systems and devices, that orient configured electrical fields to specific points, preferentially directing current a targeted cellular region and facilitating the clinical effect. The best direction of the shaped current can be determined intra-operatively through recordings and clinical testing along the "X-Y" plane.

An eighth objective of the present invention is to use shaped electrodes in deep brain stimulation (DBS) methods, systems and devices, in order to decrease off-target current stimulation, thereby minimizing or eliminating exposure to adjacent cellular regions that produce side effects.

A ninth objective of the present invention is to use the decreased electrical "aperture" of shaped electrodes in deep brain stimulation (DBS) methods, systems and devices, in order to maintain current density on the target region, but with less overall current flow and less battery drain over time.

Methods, systems and devices are provided for deep brain stimulation (DBS), that can include providing a pulse stimulator with battery supply and controls within one unit, imbedding the single unit on a head of a user, and generating a single treatment pulse from the stimulator to the brain of the user, the single pulse being generated on demand of a sensed initiation of an impulse burst from a condition. Another single pulse can be generated upon occurrence of a follow-up sensed impulse burst. The impulse bursts can come from a detected brain activity condition such as those associated with tremors, and the like.

The methods, systems and devices can also include providing the battery power supply solely in a compact skull-mounted cylindrical disc cap without implanting of batteries in a chest area of the user and avoiding any use of wires under skin from the chest area to connect to the stimulator, mounted as a skull cap with the top cap disc cover and the bottom cylindrical disc housing underneath and covered by the scalp, with a single opening in the skull for the lead line, further improving patient comfort.

Controls can also include filtering sensed signals from electrode sensors to a noise amplitude filter, followed by counting impulses in the filtered signals with an impulse counter, and then triggering the single treatment pulse when a selected threshold of the counted impulses has been reached. Furthermore, controls can allow for shutting off the noise amplitude filter, and the impulse counter when the triggering of the single treatment pulse has been initiated.

Various types of directional components can be provided for directing the treatment signals to effected areas of the brain of the user.

Further objects and advantages of this invention will be apparent from the following detailed description of the presently preferred embodiments, which are illustrated schematically in the accompanying drawings.

BRIEF DESCRIPTION OF THE FIGURES

FIG. 5a shows an open view of a miniaturized integrated battery/stimulator apparatus of the subject invention.

FIG. 5b shows a closed view of the apparatus of FIG. 5a.

FIG. 7a shows enlarged side views of four shaped electrodes with projected fields used in the apparatus of FIGS. 5a, 5b and 6.

FIG. 7b illustrates the axial views of the four shaped electrodes of FIG. 7a with respective projected fields.

FIG. 8a shows a recording trace graph of neuronal impulse bursts in mill volts verses time that can occur with an untreated patient.

FIG. 8b shows a trace graph of associated tremor displacement for FIG. 8a in millimeters verses time that can occur with the untreated patient.

FIGS. 10, 10a and 10b shows a layout of the electronic components that can be used in the apparatus of FIGS. 5a, 5b, 6 along with the triggering algorithm of FIG. 9.

FIG. 12a shows a trace graph of the neuronal impulse bursts in milli-volts verses time of a patient being treated from being treated by the subject invention.

FIG. 12b shows a trace graph of the associated tremor displacement for FIG. 12a verses time of the patient being treated by the subject invention.

FIG. 12c shows the single pulses that occur with the subject invention technique which results in the trace graphs of FIGS. 12a-12b.

DESCRIPTION OF THE PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

This invention provides methods, systems and devices to reduce power demands substantially for DBS (deep brain stimulation), allowing for miniaturized type components to be integrated with the implanted probe(s) themselves, see FIGS. 5a, 5b, 6 and 10. The invention avoids implanting large and cumbersome card-deck size batteries in the chest area and the use of vulnerable wire leads under the skin from the chest area to connect with the implanted electrode(s) on the skull. Notably, the remote stimulator/battery with its associated wiring are the chief source of complaints in the use of this technique. Other advantages of this invention are also apparent.

The invention substantially differs from that used in current techniques. Rather than generating a continuous series of un-synchronized pulses that act whether needed or not, pulses can be generated on demand. Specifically, inhibiting pulse(s) can be interactively triggered by the onset of an unwanted electro-physiologically signaled event, such as the beginning of a tremor. The same electrode(s) that now serves as a one-way input also can serve as a bi-directional conduit to sense the electrical beginnings of the event itself as well as delivering the pulse(s). Thus, with appropriately tailored, triggering algorithms, a preferred example of which is described below in reference to FIG. 9, an inhibiting pulse can be timed for delivery so as to suppress the event's full expression.

Using this approach, power drain reductions of conservatively 85% or more are achievable, with the percentage depending on the neurological events of interest. For example, most tremors are less than approximately 10 tremor cycles per second, and can be far less when the tremor is interrupted by another intentional activity such as purposeful movement, as in the case of Parkinson's disease. Thus, the constant power drain can be reduced from approximately 150 stimulating pulses/second using the current techniques described in the prior art to now to as little as one stimulating pulse counteracting each tremor onset using interactive triggering.

Even greater power reductions are possible for "lower frequency" tremor, such as Essential tremor at approximately 5 to approximately 7 tremor cycles/second, or "low-frequency" Parkinson tremor at approximately 3 to approximately 5 tremor cycles/second.

With dramatically reduced power demands for DBS, this invention then allows for miniaturized components to be integrated with the skull cap attachment to the implanted probe(s) themselves, as shown in FIGS. 5*a*, 5*b*, 6 and 10.

Figure 1:
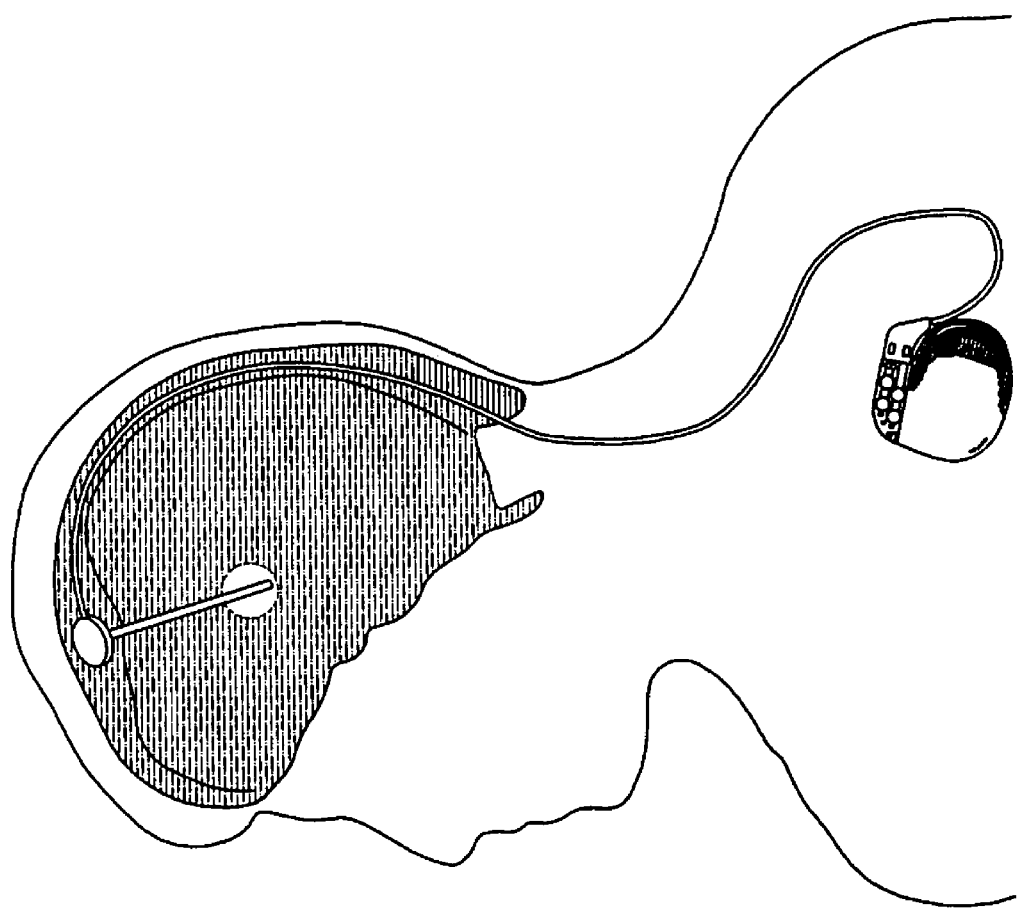
FIG. 1 shows a deep brain stimulation (DBS) apparatus of the prior art.
Figure 2:
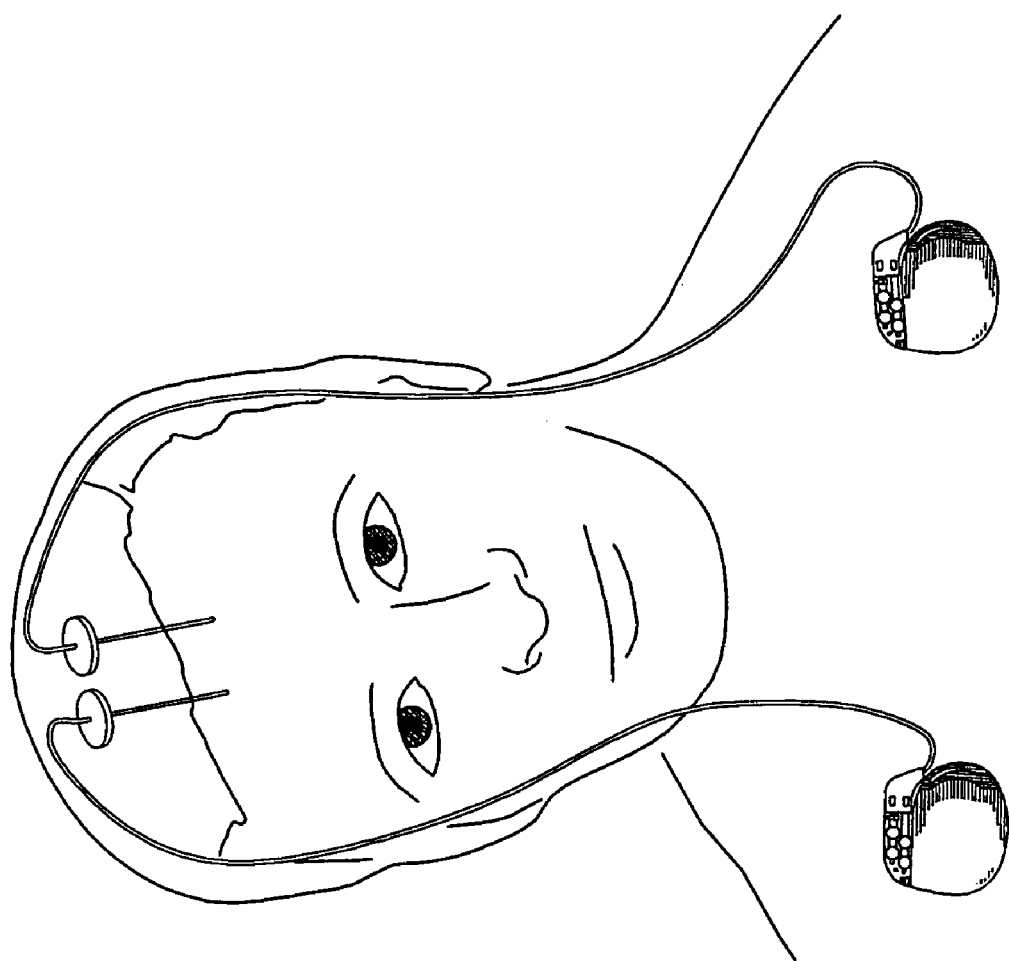
FIG. 2 is a front view of the current prior art DBS of FIG. 1.
Figure 3:
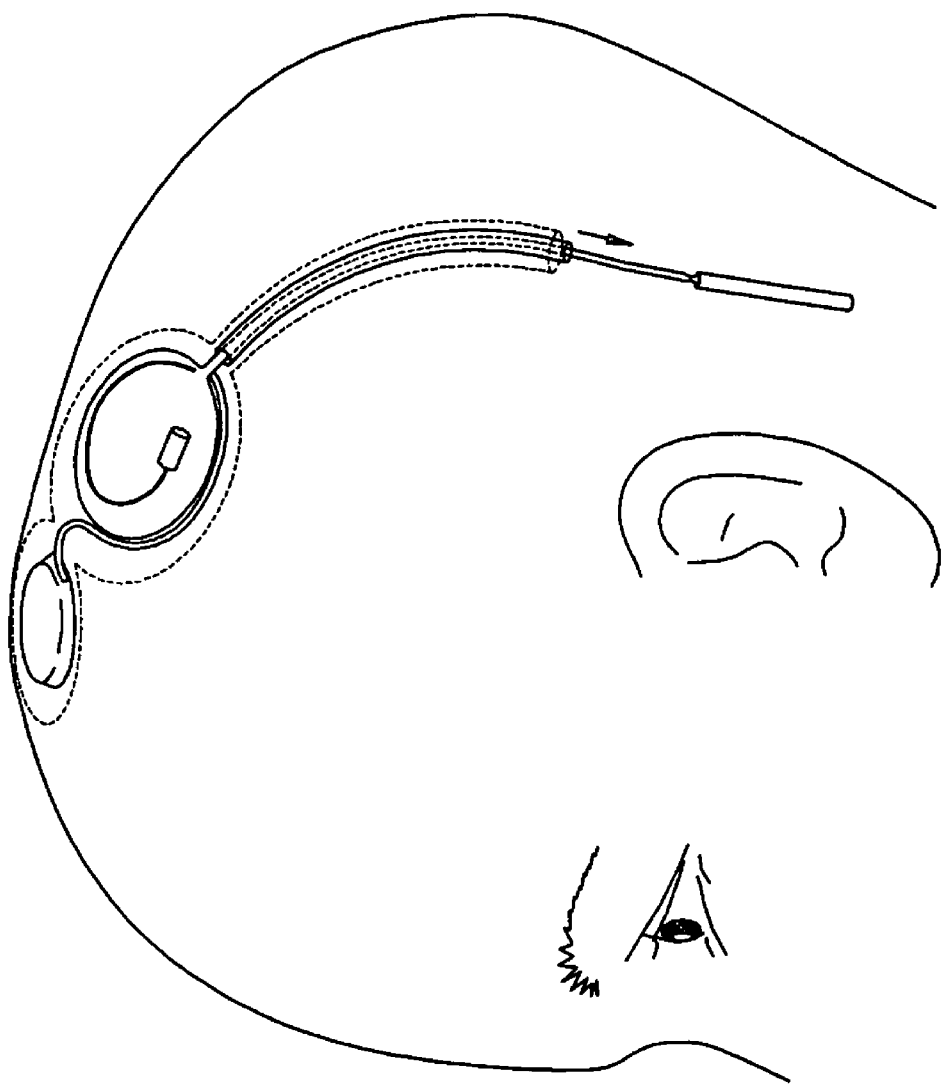
FIG. 3 shows DBS head-mounting details of the prior art of FIGS. 1-2.
Figure 4:
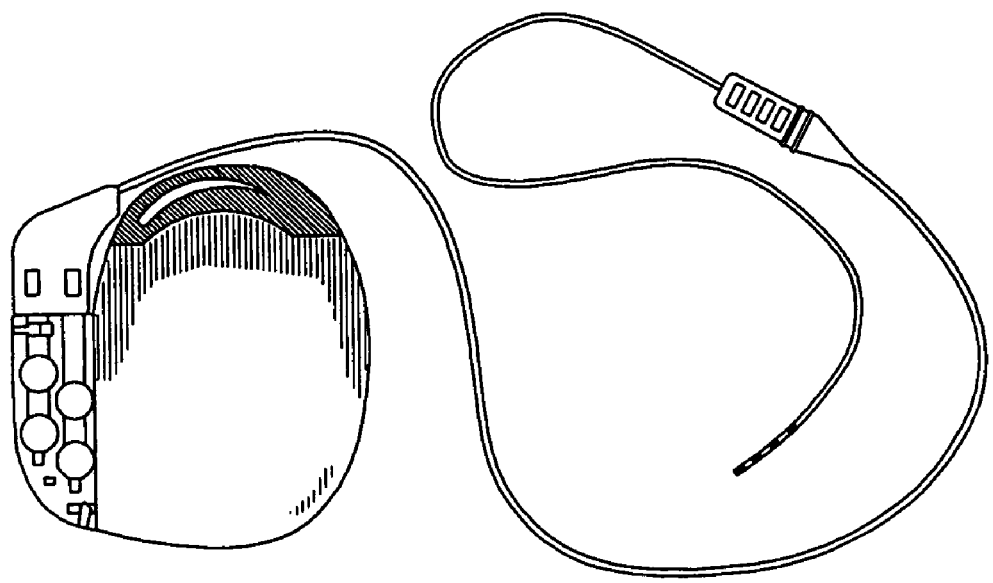
FIG. 4 shows another prior art product device.
Figure 6:
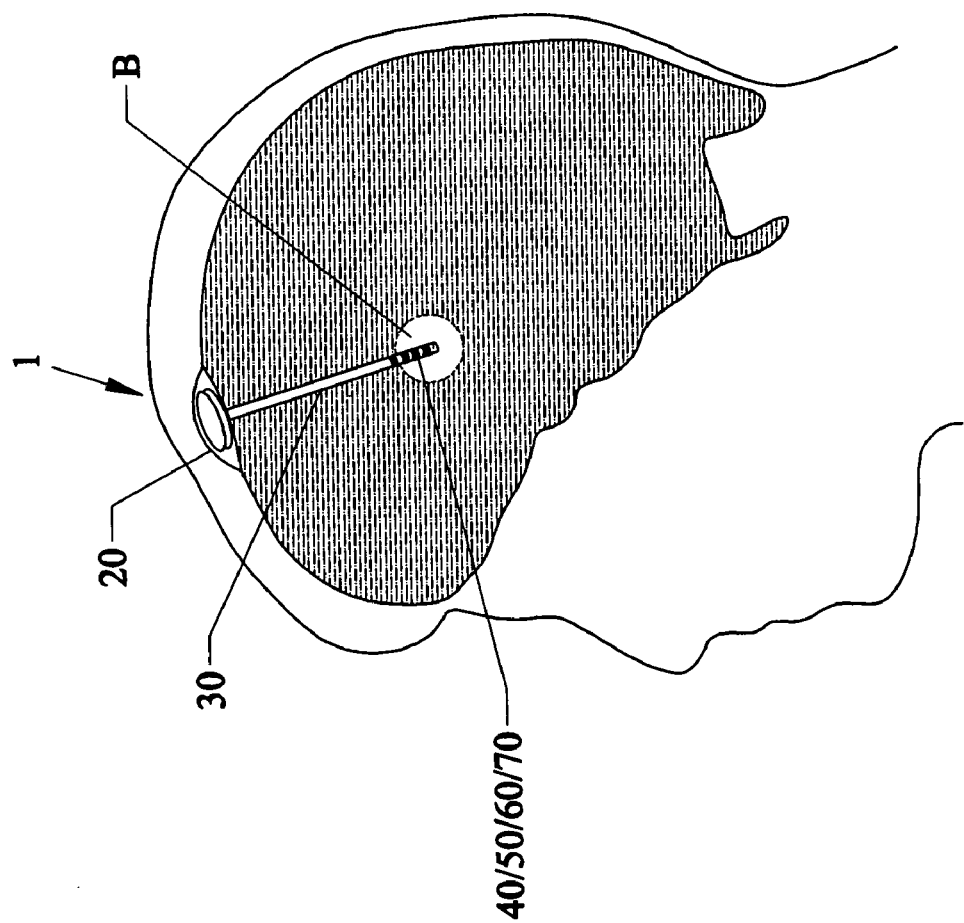
FIG. 6 shows the novel invention apparatus of FIGS. 5a-5b utilized in a head mounted application.

FIG. 5*a* shows an open view of a miniaturized integrated battery/stimulator apparatus 1 of the subject invention. FIG. 5*b* shows a closed view of the apparatus 1 of FIG. 5*a* in a cylindrical disc housing where the top cap covers the bottom cylindrical disc of the disc housing. FIG. 6 shows the novel invention apparatus 1 of FIGS. 5*a*-5*b* utilized in a head mounted application with the top cap disc cover and the bottom cylindrical disc housing mounted as a skull cap underneath and covered by the scalp with the imbedded probe extending downward from beneath a central portion of the cylindrical housing through the skull and into the brain. As shown in FIG. 6, the novel size of the cylindrical disc housing and the cap mount application is compact and easier to use than the prior art, and is not uncomfortable and cumbersome to the user as in the prior art. The compact cylindrical disc housing with miniaturized components does not cause a noticeable protrusion above the scalp line and existing hair of the user.

Referring to FIGS. 5*a*-5*b* and 6, the hole cap 20 can include a top cover 20T, and bottom cylindrical disc housing 20B to house components 100 (which are described and shown in greater detail in reference to FIG. 10). Underneath the cap 20 can be a lead line 30, and approximately four (4) directional electrodes 40, 50, 60 and 70 attached thereon. FIG. 7*a* shows enlarged side views of four shaped electrodes with projected fields used in the apparatus of FIGS. 5*a*, 5*b* and 6. FIG. 7*b* illustrates the axial views of the four shaped electrodes of FIG. 7*a* with respective projected fields.

Referring to FIGS. 6, 7*a* and 7*b*, the electrodes 40-70 on the lead 30 can include a non-conducting material, such as but not limited to insulating material, and the like, on one side or on a portion of the electrode. Examples, of non-conducting material can include but are not limited to rubbers, elastomers, plastics, coated metals, and the like, and combinations thereof, and the like.

This nonconductive material can also be used to help direct electrical field emissions to one side or to more specific regions, and/or points, rather than to a 360-degree emission. The invention can include a lead 30 can having a single electrode with a nonconductive surface region.

Alternatively, more than one electrode can be used on the lead in series to one another. The nonconductive surface region can be applied on the same side of the electrodes, or to different side surface portions of the electrodes as needed. Additionally, different combinations can be used. For example, an upper electrode can emit up to 360 degrees while other electrodes are directed to emit in specific regions and/or points.

Additionally, circuitry can be added to control which electrodes are being emitted at selected time periods, and the like. For example, electrodes can be further programmed with a microprocessor, to activate simultaneously and/or sequentially, and/or staggered and/or over different combinations, and the like. The invention can use directional type electrodes, such as those shown and described in reference to U.S. Published Patent Application 2002/0183817 to Van Venrooij et al., which is incorporated by reference.

The miniaturized implantable electrode apparatus and stimulation systems can also include those described in U.S. Patent Application 20030023297, to Byers et al. filed on Jan. 30, 2003, which is incorporated by reference. This reference describes an eyelid stimulation system and circuitry that causes a paralyzed eyelid to close or open by passing an electrical stimulating current to a nerve.

The invention can be used to treat brain impulse bursts and the resultant physical extremity tremors that result therefrom. FIGS. 8*a* and 8*b* represent untreated brain impulse bursts and resultant physical extremity tremor outcome that are untreated. FIG. 8*a* shows the recording of impulse bursts from the brain B, that results from the leads 30 that are connected to the electrodes 40-70 (of the apparatus of FIG. 6). The large amplitude bursts represent the impulses that result in the tremors (impulses from brain to effected extremity). FIG. 8*b* represents an extremity that is being affected by the impulse (here for example, a single index right hand finger). A laser measuring sensor was aimed at the index finger to record the results shown in FIG. 8*b*. For example, a plus 5 mm apex reading would represent the finger moving forward from a horizontal plane, and −5 mm represents the finger moving aft in the horizontal direction.

Figure 9:
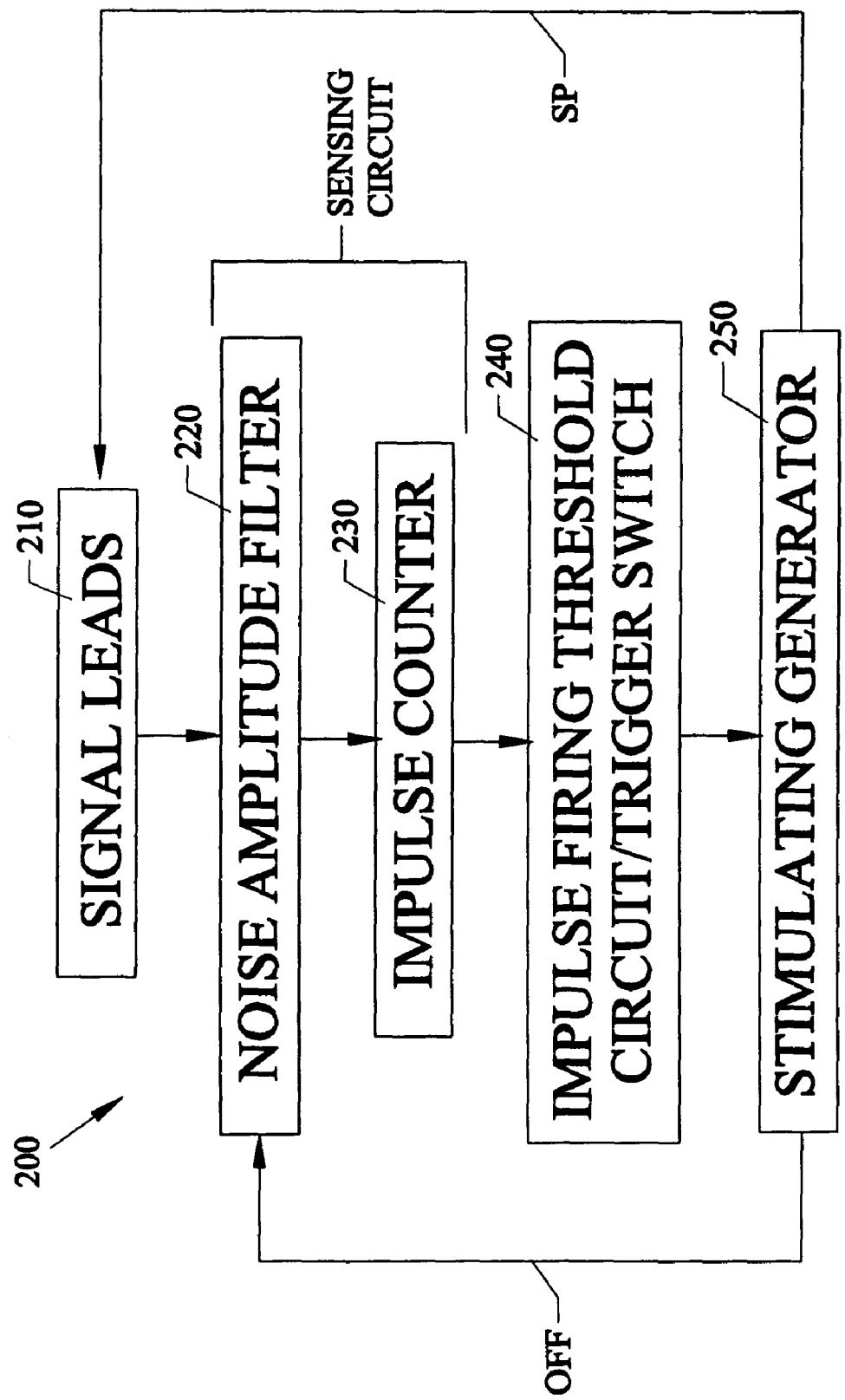
FIG. 9 shows an exemplary flow chart of a triggering algorithm steps that can be used with the invention.

The invention can use a triggering algorithm to selectively activate electrodes and treat effected parts of the brain where impulse bursts occur. FIG. 9 shows an example flow chart of a triggering algorithm steps that can be used with the invention. The triggering algorithm can take a number of forms or be adaptive, based on patient neuro-generative responses. In a simple illustrative form, not intended to be limiting, triggering sensing can be based on exceeding a threshold-firing rate measured in impulses/second.

FIG. 9 shows an exemplary triggering algorithm 200 for using the electrodes 40-70 of the preferred embodiment shown in the preceding figures that switches back and forth between a sensing mode and transmitting mode. In the first step 210, signals coming from leads 30 from the microelectrodes 40-70 in the implant receive a signal from the electrodes 40-70 (the first left trace signal from FIG. 8*a*) can be passed through a noise amplitude filter 220 (for example an high pass amplitude filter cutting off a low frequency of for example everything below approximately 20 mill volts is filtered out). Next during step 230, the filtered signal goes to an impulse counter, such as a clock counter which can count the number of impulses passing through, which can be represented in impulses per second. Next step 240, has an impulse firing threshold type circuit that can be used that filters out false alarms and allows for a selected threshold, such as for example, 5 impulses within 50 milli-seconds, would trigger the generator in step 250 to send a generated pulse SP back down the signal leads 30 to the electrodes 40-70.

When the generator is triggered, a signal can also be sent (along line Off) to simultaneously shut off the sensing mode of the electrodes, allowing the electrodes to be in a transmitting mode state. Sensing mode parameters of the electrodes 40-70 can be in approximately 20 to approximately 60 millivolts, while the transmitting/triggering range of the electrodes 40-70 can be approximately 2 to approximately 4 volts. The novel triggering algorithm 200 allows the electrodes 40-70 to be switched back and forth between transmitting and sensing modes without overloading the circuit components, and thus maximizing power usage during operation.

Once triggered, stimulation blocking continues until firing impulse firing rate drops below the critical threshold value. The sensing and stimulation can use the same micro-electrode leads, alternatively, wherein the sensing circuitry first uses an impulse counter/clock, then if threshold is exceeded, circuit switching turns "off" the sensor and turns "on" the stimulator for one or more pulses.

Various triggering algorithms can be developed for effective symptom suppression with animal studies. However, the safety of this invention's procedure has already been established for humans with continuous and higher pulse rates through FDA (Food and Drug Administration) approval. Further, a market also exists for electronic retrofit to thousands of patients who have already been implanted previously, without further brain surgery since the existing DBS electrodes can serve as a two-way bi-directional conductor.

In vitro testing of this approach also can be possible using current systems by sensing electro-magnetic forces from subcutaneous wires of a neurological event onset, such as the beginning of a tremor. These signals, then in turn, can allow the triggering of the existing magnetic switch for turn "off" and "on."

Other types of triggering mechanisms can include those described in U.S. Pat. No. 6,539,263 to Schiff; U.S. Pat. No. 6,366,813 to DiLorenzo; U.S. Pat. No. 6,301,492 to Zonenshayn; U.S. Pat. No. 6,038,480 to—Hrdlicka et al.; U.S. Pat. No. 5,833,709 to Rise et al.; U.S. Pat. No. 5,716,377 to Rise et al.; and U.S. Pat. No. 5,707,396 to Benabid, which are all incorporated by reference. Additionally, U.S. Patent Applications 20030181954 to Rezai; 20030085684 to Tsukamoto et al.; and 20020188330 to Frans et al., which are all incorporated by reference, FIGS. 10, 10*a* and 10*b* shows a layout of the electronic components that can be used in the apparatus of FIGS. 5*a*, 5*b*, 6 along with the triggering algorithm of FIG. 9. Referring to FIGS. 5*a*, 5*b*, 6, 10, 10*a* and 10*b*, the cap 20 can include miniaturized components that include a battery type power supply 110, which provides power to a stimulation generator controller 120, which is triggered by a triggering switch 250 which receives signals from a sensing circuit 140 all of which are connected to electrodes 40-70 on lead line 30 that is implanted into the skull 310 of the patient 300.

The invention can make use of ultra-miniature batteries 110 such as those, manufactured by Advanced Bionics Corp., which are only about ⅕₅ the size of a standard AA battery and now serve medical implants by emitting electrical micropulses that stimulate nearby nerves. These tiny batteries, or "Bions," can also be can be programmed from outside the body for strength and frequency of the stimulation, and wirelessly recharged with an electrical field. The use of these ultra-miniature batteries would avoid both a chief source of complaints; the remotely implanted card-deck sized stimulator/battery [about 60 by about 80 by about 15 mm] in the chest area, its replacement, while also avoiding problems associated with vulnerable wire leads under the skin from the chest area to connect with the implant on the skull.

The Stimulation Generator Controller 120 can be a solid-state device such as the one shown and described in the Medtronic's Model 3628 cited 0093 of U.S. Published Patent Application No. 2002/0183817 to Van Venrooij et al., which is incorporated by reference. Trigger Switch 130 can be a common mini-double throw "on-off" and "off-on" electronic switch, triggering based on sensing circuit threshold. The Sensing Circuit 140 can be a common solid-state impulse counter-clock, e.g. mini-version of cardiac-alarm, monitoring electrical impulses to heart The circuits are powered by miniature battery 110 as shown in FIG. 10*b*. The sensing circuit 140 can include the noise amplitude filter 220 and impulse counter 230 of FIG. 9. The trigger switch 130 is activated when threshold circuit 240 of FIG. 9 is exceeded to turn "off" the sensor input and turn "on" the stimulation generator 120. This is reversed when the impulse is blocked, dropping below threshold.

The components to run the novel invention can be fit into a space of approximately 60 mil by 15 mil compared to prior art. Conservatively less than 50% of the current 60 by about 80 by about 15 mm in a plastic skull-cap implant see FIG. 6.

The invention can be less expensive than the current techniques, since no surgery tunneling down the neck into the chest area is needed for the battery cards, and thus no repairs or surgery for those components—which currently about $10,000 every 3-5 years.

Benefits of using the novel triggering algorithm of FIG. 9 and apparatus components of FIGS. 5*a*, 5*b*, 6, 10 and FIGS. 11*a*-11*c*, 12*a*-12*c*.

Figure 11C:
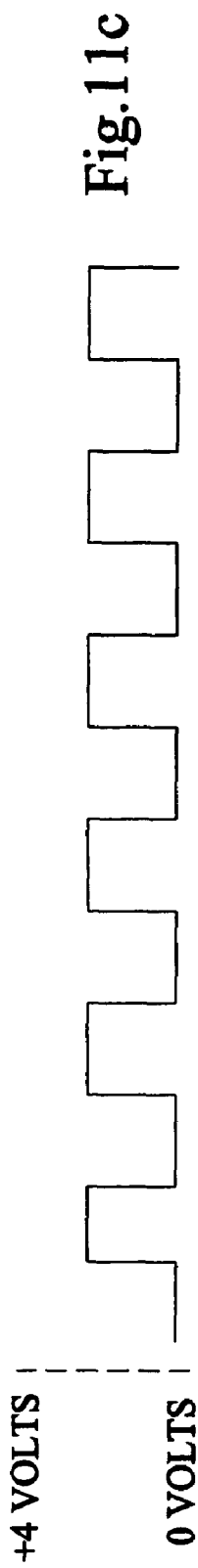
FIG. 11c shows the continuing pulse train that occurs with the Medtronic type (prior art) technique which causes the trace graphs of FIGS. 11a-11b.
Figure 11A:
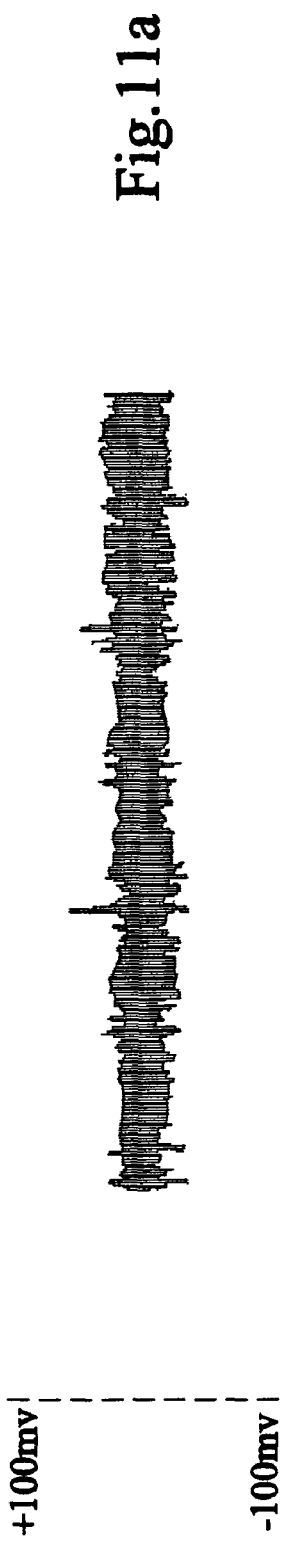
FIG. 11a shows a trace graph of the neuronal impulse bursts in milli-volts verses time of a patient being treated with a Medtronic type (prior art) technique.
Figure 11B:
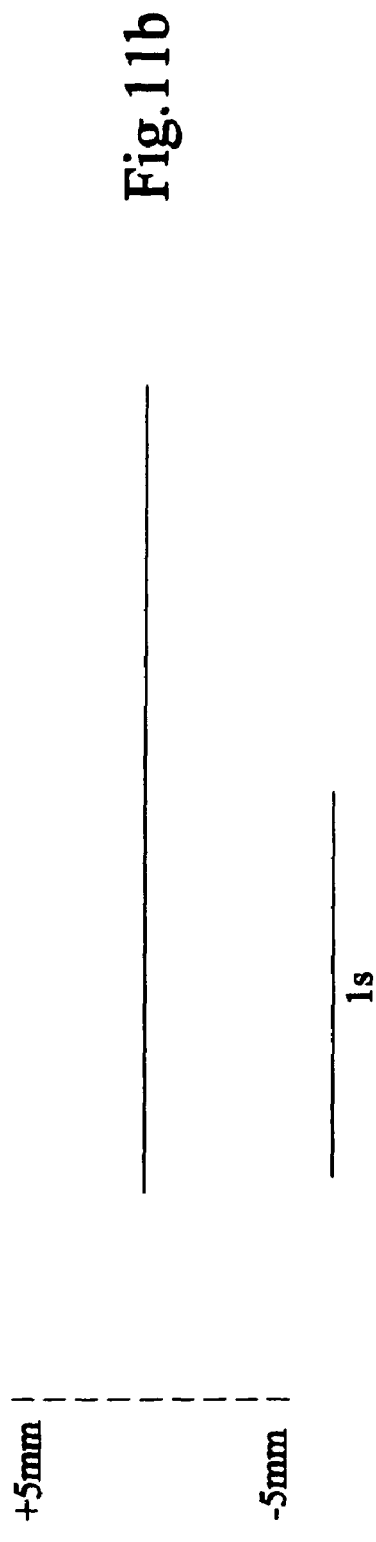
FIG. 11b shows a trace graph of the associated tremor displacement for FIG. 11b verses time of the patient being treated with the Medtronic type (prior art) technique.

FIG. 11*a* shows a trace graph of the neuronal impulse bursts in mill volts verses time of a patient being treated with a Medtronic type (prior art) technique such as the one shown and described in reference to U.S. Patent Application Publication 2002/0183817 to Van Venrooij et al., which is incorporated by reference. FIG. 11*b* shows a trace graph of the associated tremor displacement for FIG. 11*b* verses time of the patient being treated with the Medtronic type (prior art) technique. FIG. 11*c* shows the continuing pulse train that occurs with the Medtronic type (prior art) technique which causes the trace graphs of FIGS. 11*a*-11*b*.

Referring to FIGS. 11*a*-11*c*, results in a continuing pulse train (FIG. 11*c*) in order to cause the effects of no impulse bursts (FIG. 11*a*) and no resultant physical tremors (FIG. 11*b*). As described in the background section of this invention this technique requires continuously generating pulsed type signals once the electrodes are activated whether or not a brain type tremor has ended, which would result in needless and excessive, unwanted and potentially dangerous electrical current being continuously generated inside the brain. The more unnecessary pulse type signals, the more undesirable side effects to the patient.

Additionally, the technique proposed in this patent application publication would require excessive power to operate, which are not only expensive since battery power supplies would need to be constantly replaced but also require large card size batteries that must be externally mounted outside of a patient or mounted inside of the upper chest or be constantly connected to an external power supply. This proposed Medtronic technique would also be prone to short circuit since the electrodes would be simultaneously operating as both transmitters and sensors, which also causes excessive and unnecessary power drain, which also shortens the lifespan of any batteries being used as well as increase the costs for replacing the batteries.

FIG. 12*a* shows a trace graph of the neuronal impulse bursts in mill volts verses time of a patient being treated from being treated by the subject invention described above. FIG. 12*b* shows a trace graph of the associated tremor displacement for FIG. 12*a* verses time of the patient being treated by the subject invention. FIG. 12*c* shows the single pulses that occur with the subject invention technique which results in the trace graphs of FIGS. 12*a*-12*b*.

Referring to FIGS. 12a-12c, the invention causes single spaced apart pulses to occur over greater periods of time, where each pulse occurs on-demand, and not as a continuous series of pulses. As shown by FIG. 12a, the initial impulse burst and subsequent impulse bursts have long delay time periods there between, which can result in substantially reduced or eliminated tremors resulting therefrom, FIG. 11b.

The novel invention allows for less undesirable electrical current to be generated within the brain, less side effects that result therefrom, less power consumption as well as other apparent benefits. The novel invention can use small batteries that were not able to be used in the prior art systems and techniques, and also results in power supplies that require less replacements as well. The novel invention is able to eliminate the need for large and cumbersome card type batteries or external power supplies, and results in a better system for treatment.

Differences between the subject invention and that described in the Medtronic technique shown in U.S. Patent Application Publication 2002/0183817 to Van Venrooij et al. are compiled in Table 1.

TABLE 1

Comparison of prior art(Medtronic) and Invention.

| Attribute | Medtronic | Invention |
|---|---|---|
| Sensing | Loss of Effectiveness | Single Event |
| Trigger | Brain "Activity" | Initial Impulse Burst |
| Objective | Select Electrodes | Stop Single Tremor |
| Stimulator | Normally-On | Normally-Off |
| Power | No "off" (continuing pulses) | Only "on" as needed (individual pulse) |
| | Large Battery | Small Battery |
| Power Lifespan | Limited | Extended |
| Battery Mounting | "Implantable" | Skull-Mounted in Cap |
| Side Effects | Continuous electrical current | Limited Electrical Current |

Besides circuitry miniaturization, by triggering pulse generation only when needed, fewer pulses per second also can reduce some of the mild, but known side effects of DBS, and the timed delivery also can delay the onset of the next event by physiological feedback, that is also known to be effective against a known clinical phenomena Parkinson's Disease.

Other advantages can also be realized. The timed pulse feedback speculatively could induce the brain to adaptively alter actual neural circuitry, allowing a further reduction of pulse rate and even more efficiency or even better help reduce symptoms naturally, just as brain circuitry is known to be altered by experience.

While the invention has been described for use with tremors, the invention can have applicability to other medical applications, such as but not limited to movement disorders and cardiac dysfunctions, but extends to include other neurological diseases and disorders such as epilepsy, psychiatric and behavioral dysfunctions such as schizophrenia and drug-induced symptoms and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method for providing deep brain stimulation (DBS), consisting of the steps of:

providing an implantable pulse stimulator with battery supply and miniaturized controller within one single self-contained elongated probe for sensing and stimulating to eliminate spatially separated detection and stimulation electrodes, the providing step includes:
fabricating a single implantable lead line for implanting in the head of a patient below their skull;
attaching four electrodes to an exterior surface of the single implantable lead line for sensing and transmitting for both sensing and stimulating, wherein one of the four electrodes emits in an approximately 360 degree field about the implantable lead line, and the other electrodes emit in selected directional regions;
forming a single cylindrical disc housing, the single cylindrical disc housing containing components that fit into a space of approximately 60 millimeters in diameter by approximately 15 millimeters in height;
extending the single implantable lead line beneath a center portion of the single cylindrical disc housing;
enclosing the battery supply and the miniaturized controller as the components inside a compartment of the single cylindrical disc housing without implanting any batteries in a chest area of a user and avoiding use of any wires under skin from the chest area to connect to the stimulator, the compartment in the cylindrical disc housing contains a hole with the components arranged around the hole;
internally connecting the electrodes through the single implantable lead line to the controller located inside of the cylindrical disc housing; and
forming a top disc cover having perimeter side edges;
covering the compartment in the cylindrical disc housing with the top disc cover having the perimeter side edges;
producing a fully enclosed single self-contained deep brain simulation probe with both the cylindrical disc housing, the top disc cover and the single lead line so as to avoid the risk of implanting more than one single probe into different spatially separated areas of the brain;
imbedding only the single implantable lead line which extends beneath the one single self-contained probe below a single opening in the skull of the user into one single area of a brain as a self-contained bi-directional conduit for deep brain stimulation;
capping the skull with the single cylindrical disc housing and the top disc cover so that the single cylindrical disc housing with the top disc cover is positioned as a cap on top of the skull above the single opening in the skull;
covering the cylindrical disc housing and the top disc cover with the scalp so that the height of the cylindrical disc housing and the top disc cover protrudes so as to not cause a noticeable protrusion on the head of the user;
sensing an initiation of an unwanted electro-physiologically signaled event of an impulse burst in an area of the brain of the user caused by a condition using one of the electrodes, wherein the sensing of the initiation includes the steps of:
filtering sensed signals of the impulse burst from the one electrode to a noise amplitude filter;
counting impulses in the filtered signals with an impulse counter; and
triggering the single treatment pulse when a selected threshold of the counted impulse has been reached; and
selectively generating a single treatment pulse only from the one electrode to only the area of the brain of the user, the single pulse being selectively generated on demand of the sensed initiation of unwanted electro-physiologically signaled event of the impulse burst caused by the condition without user intervention, the sensing and stimulating of the electrodes being alternatively active.

2. The method of claim 1, wherein the step of generating includes generating a non-continuous spaced apart pulse upon occurrence of a follow-up sensed impulse burst.

3. The method of claim 1, wherein the condition includes: a tremor.

4. The method of claim 1, wherein the providing step includes:
providing a processor based controller for executing
a set of monitoring instructions for sensing initiation of an unwanted electro-physiologically signaled event, and
a set of triggering instructions for activating the stimulator to generate the single treatment pulse, the monitoring and sensing being alternately activated.

5. Thu method of claim 1, wherein the sensing step includes
sensing modes in the electrodes between approximately 20 to approximately 60 milli-volts, and
triggering the electrodes between approximately 2 to approximately 4 volts, wherein
the electrodes switch back and forth between sensing and triggering modes without overloading circuit components, and thus maximizing power usage during operation.

6. The method of claim 1, wherein the filtering step includes
filtering out false alarms and allowing for a selected threshold value with an impulse firing threshold circuit.

7. The method of claim 6, wherein the threshold value includes approximately 5 impulses within approximately 50 milli-seconds.

8. The method of claim 1, wherein the enclosing the battery step includes
wirelessly recharging the battery supply by an external electric field.

9. The method of claim 1, wherein the sensed impulse burst includes a tremor of approximately 5 to approximately 7 tremor cycles per second.

10. The method of claim 1, wherein the sensed impulse burst includes a tremor of approximately 3 to approximately 5 tremor cycles per second.

11. A method for providing deep brain stimulation (DBS), consisting of the steps of:
providing a single lead line having a plurality of electrodes, wherein each of the electrodes alternate from being a detection electrode and a stimulation electrode, the single lead line having a diameter;
providing a single cylindrical disc housing, having components that fit within a space of approximately 60 millimeters in diameter by approximately 15 millimeters in height;
housing a battery supply and a controller for controlling the detection electrode and stimulation electrode inside a compartment in the single cylindrical disc housing, the compartment in the cylindrical housing contains a hole with the components arranged around the hole; within one single self-contained elongated probe for sensing and stimulating to eliminate spatially separated detection and stimulation electrodes, the providing step includes:
fabricating a single implantable lead line for implanting in the head of a patient below their skull;
covering the cylindrical disc housing with the top disc cover having perimeter side edges that cover the compartment in the cylindrical disc housing;
attaching the single lead line through a center of a bottom of the cylindrical disc housing;
imbedding only the single lead line below a single opening in the skull;
capping the skull with the single cylindrical disc housing and the top disc cover so that the single cylindrical disc housing with the top disc cover is positioned as a cap mounted on top of the skull above the single opening in the skull;
covering the cylindrical disc housing and the top disc cover with the scalp so that the height of the cylindrical disc housing and the top disc cover protrudes so as to not cause a noticeable protrusion on the head of the user;
sensing an initiation of an unwanted electro-physiologically signaled event of an impulse burst in the user caused by a condition in an area of the brain using one of the plurality of the electrodes on the lead line; and
selectively generating a single treatment pulse from the one electrode to the area of the brain of the user on demand of the sensed initiation of unwanted electro-physiologically signaled event of the impulse burst caused by the condition.

12. The method of claim 11, wherein the sensing step includes
filtering sensed signals from electrode sensors to a noise amplitude filter,
counting impulses in the filtered signals with an impulse counter, and
triggering the single treatment pulse when a selected threshold of the counted impulses has been reached.

13. The method of claim 12, wherein the sensing step includes
sensing modes in the electrodes between approximately 20 to approximately 60 milli-volts, and
triggering the electrodes between approximately 2 to approximately 4 volts, wherein
the electrodes switch back and forth between sensing and triggering modes without overloading circuit components, and thus maximizing power usage during operation.

14. The method of claim 11, wherein the filtering step includes
filtering out false alarms and allowing for a selected threshold value with an impulse firing threshold circuit.

15. The method of claim 14, wherein the threshold value includes approximately 5 impulses within approximately 50 milli-seconds.

16. The method of claim 14, wherein the housing the battery supply step includes
wirelessly recharging the battery supply wireless by an external electric field.

17. The method of claim 11, wherein the sensed impulse burst includes a tremor of approximately 5 to approximately 7 tremor cycles per second.

18. The method of claim 11, wherein the sensed impulse burst includes a tremor of approximately 3 to approximately 5 tremor cycles per second.

* * * * *